(12) United States Patent  (10) Patent No.: US 6,641,692 B2
Reynolds et al.  (45) Date of Patent: Nov. 4, 2003

(54) METHOD OF MAKING AN ABSORBENT ARTICLE HAVING LEG CUFFS COMBINED WITH CONTAINMENT FLAPS

(75) Inventors: Gary Mack Reynolds, Neenah, WI (US); Robert Eugene Vogt, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/074,147

(22) Filed: Feb. 11, 2002

(65) Prior Publication Data

US 2002/0074079 A1 Jun. 20, 2002

Related U.S. Application Data

(60) Continuation of application No. 09/122,432, filed on Jul. 24, 1998, now Pat. No. 6,346,162, which is a division of application No. 08/777,685, filed on Dec. 20, 1996, now Pat. No. 5,827,387.

(51) Int. Cl.[7] .............................................. B32B 31/08
(52) U.S. Cl. ...................... 156/164; 156/179; 156/202; 156/216; 156/229; 156/259
(58) Field of Search ................................. 156/73.1, 495, 156/164, 229, 163, 270, 178, 179, 202, 216, 259, 560, 176; 604/385.2, 358, 365, 366, 385.01, 385.03, 385.04, 385.24, 385.27, 385.28

(56) References Cited

U.S. PATENT DOCUMENTS

| | | | | |
|---|---|---|---|---|
| 4,081,301 A | 3/1978 | Buell | ......................... | 156/164 |
| 4,239,578 A | 12/1980 | Gore | ......................... | 156/361 |
| 4,695,278 A | 9/1987 | Lawson | .................. | 604/385 A |
| 4,795,454 A | 1/1989 | Dragoo | ..................... | 604/385.2 |
| 4,808,177 A | 2/1989 | DesMarais et al. | ....... | 604/385.1 |

(List continued on next page.)

FOREIGN PATENT DOCUMENTS

| | | | |
|---|---|---|---|
| EP | 0 528 282 A2 | 2/1993 | ........... A61F/13/15 |
| EP | 0 532 034 A2 | 3/1993 | ........... A61F/13/15 |
| WO | WO 94/18927 | 9/1994 | ........... A61F/13/15 |
| WO | WO 95/34265 | 12/1995 | ........... A61F/13/15 |
| WO | WO 96/19166 | 6/1996 | ........... A61F/13/15 |
| WO | WO 96/24319 | 8/1996 | ........... A61F/13/15 |

*Primary Examiner*—Jeff H. Aftergut
*Assistant Examiner*—Gladys Corcoran
(74) *Attorney, Agent, or Firm*—Wilhelm Law Service (57) ABSTRACT

The invention relates to methods of fabricating an absorbent article. In one method of the invention, combination containment flaps and leg cuffs are formed on a common substrate. A plurality of elastomeric elements are included in the combination article to assist in forming containment flaps. Discrete leg cuff pieces are applied to the substrate at longitudinally spaced locations. In some embodiments, a cutting device slits the substrate substantially along a center line extending the length of the substrate, forming two continuous substrate portions. A glue gun applies adhesive to the substrate portion. The substrate portions are folded lengthwise, using the adhesive to form integral containment flaps and leg cuffs in a composite substrate. The composite substrate is secured to an absorbent article web sausage in forming absorbent articles. In another embodiment, the substrate is a first substrate which supports elastomeric elements used in forming leg cuffs and containment flaps. The first substrate is secured to a second substrate, thus forming a base structure, with the elastomeric elements between the first and second substrates. A bodyside liner and an absorbent core are added on one side of the base structure, and an outer cover is added on the second side, to form a web sausage. In both embodiments the web sausage is cut transversely at spaced locations along the length of the web sausage, to form absorbent articles.

13 Claims, 8 Drawing Sheets

U.S. PATENT DOCUMENTS

| | | | |
|---|---|---|---|
| 4,816,025 A | 3/1989 | Foreman | 604/385.2 |
| 4,822,435 A | 4/1989 | Igaue et al. | 156/164 |
| 4,834,740 A | 5/1989 | Suzuki et al. | 604/385.2 |
| 4,892,528 A | 1/1990 | Suzuki et al. | 604/385.2 |
| 4,900,384 A | 2/1990 | Sanders et al. | 156/204 |
| 4,940,464 A | 7/1990 | Van Gompel et al. | 604/396 |
| 5,030,303 A | 7/1991 | Cucuzza | 156/164 |
| 5,032,120 A | 7/1991 | Freeland et al. | 604/385.2 |
| 5,064,489 A | 11/1991 | Ujimoto et al. | 156/164 |
| 5,085,724 A * | 2/1992 | Focke | 156/256 |
| 5,137,526 A | 8/1992 | Coates | 604/391 |
| 5,167,653 A | 12/1992 | Igaue et al. | 604/385.2 |
| 5,190,606 A | 3/1993 | Merkatoris et al. | 156/164 |
| 5,292,316 A | 3/1994 | Suzuki | 604/385.2 |
| 5,330,598 A | 7/1994 | Erdman et al. | 156/164 |
| H1420 H | 2/1995 | Richardson | 604/385.2 |
| 5,421,924 A | 6/1995 | Ziegelhoffer et al. | 156/73.1 |
| 5,454,803 A | 10/1995 | Sageser et al. | 604/385.2 |
| 5,476,458 A | 12/1995 | Glaug et al. | 604/378 |
| 5,660,666 A * | 8/1997 | Dilnik et al. | 156/259 |

* cited by examiner

METHOD OF MAKING AN ABSORBENT ARTICLE HAVING LEG CUFFS COMBINED WITH CONTAINMENT FLAPS

This application is a continuation of application Ser. No. 09/122,432, filed Jul. 24, 1998, now U.S. Pat. No. 6,346,162, which is a divisional application of Ser. No. 08/777,685, filed Dec. 20, 1996 now U.S. Pat. No. 5,827,387.

FIELD OF THE INVENTION

The present invention relates to methods for fabricating absorbent articles. Such methods usually include gluing and may include ultrasonic bonding, to combine elements and form absorbent articles.

BACKGROUND OF THE INVENTION

Conventional methods of making absorbent articles, such as disposable diapers, are well known in the art. These methods usually rely on attaching leg cuffs, containment flaps, and other elements to the absorbent article as continuous webs of attachment material. Thus a continuous strip of material, such as leg cuff material, is continuously applied to the shell of an absorbent article. This method allows for high speed forming of absorbent articles.

Applicants' process greatly reduces the complexity by placing leg cuffs and containment flap elastomeric elements on a continuous web or substrate. The continuous web is slit and folded to create two combined leg cuffs and containment flaps, and is then secured to an absorbent article web sausage.

By forming the leg cuffs and containment flaps separately from the web sausage, the number of processing steps or operations to the web sausage is reduced. This can increase the throughput speed of the manufacturing process.

Another of applicants methods forms the combined leg cuff and containment flaps on a substrate and then secures an outer cover to a first side of the substrate and a bodyside liner and absorbent core to a second side of the substrate, thus forming a further unique absorbent article.

SUMMARY OF THE DISCLOSURE

The present invention relates to methods for fabricating absorbent articles, and focuses on forming leg cuffs and containment flaps. More particularly, the methods include applying elastomeric elements to a continuous web substrate and applying leg cuffs at longitudinally spaced locations along the substrate. The leg cuffs are transversely spaced from the elastomeric elements. One method further includes slitting the continuous web along its length at a center line to form two continuous web substrate portions, each having the leg cuffs and the elastomeric elements. The two continuous web portions are folded to form respective composite substrates of containment flap material, with leg cuffs spaced along the length of the containment flap material. The integral leg cuffs and containment flaps are then applied to a web sausage.

In one embodiment, opposed pairs of leg cuff pieces are longitudinally spaced along the length of each of the respective composite substrates. The opposed pairs of leg cuff pieces are disposed between the outer edges of the respective composite substrates and longitudinally extending elastomeric elements on the respective composite substrate.

In another embodiment the extensible leg cuffs are stretched, preferably to a dimension representing about 20% to 50% of the respective stretch-to-stop distance, when secured to the substrate.

In yet another embodiment, the leg cuff pieces comprise elastomeric strands secured to a generally nonelastomeric piece of material.

In still another embodiment, the leg cuff pieces, when secured to the substrate, substantially cover the leg cut-cuts.

Another embodiment includes the step of applying ultrasonic energy to the respective composite substrates to finish and smooth raw edges thereon.

In a further embodiment adhesive is applied along a center line of the respective composite substrate before mounting to the web sausage.

In a still further embodiment adhesive is applied along the longitudinal outside edge of the respective composite substrate adjacent respective leg cuff pieces before application to the web sausage.

In another embodiment of the invention, web structures for use as a combination leg cuff and containment flap are produced by supplying a substantially endless substrate portion having a length dimension, securing extensible leg cuff pieces to the substrate portion at longitudinally spaced locations, securing elastomeric elements longitudinally along the length dimension of the substrate portion in transversely spaced relationship to the leg cuff pieces, and folding opposing longitudinal outside edges of the substrate portion inwardly and securing the outside edges to facing portions of the substrate portion to form a composite containment flap substrate.

Another method of making an absorbent article includes securing elastomeric elements to a continuous first web substrate, slitting the substrate longitudinally to form a pair of first substrate portions, securing the first substrate portions to a second substrate, with the elastomeric elements between the second substrate and the pair of first substrate portions to form a base structure. An absorbent core and bodyside liner are applied to one side of the base structure and an outer cover is applied to the opposing side of the base structure to form a web sausage.

In one embodiment, the method includes the steps of folding outside edges of the base structure inwardly into a substantially J-shaped configuration and ultrasonically bonding the edges.

Another embodiment includes the steps of driving the base structure in a first nip at a first speed, then driving the base structure through a second nip at a second slower speed, such that ruffles are formed in the base structure between the first and second nips, the second nip securing the bodyside liner and absorbent core to the base structure while the base structure is in the ruffled condition.

The invention is not limited in its application to the details of the construction and the arrangement of the components set fort in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components.

DETAILED DESCRIPTION OF THE ILLUSTRATED EMBODIMENTS

The present invention is directed toward methods to produce absorbent articles, particularly disposable absorbent articles. The articles can be placed against or in proximity to the body of a wearer to absorb and contain various exudates discharged from the body. An exemplary method forms leg cuffs and containment flaps from a substrate comprising a continuous web of material.

Figure 1:
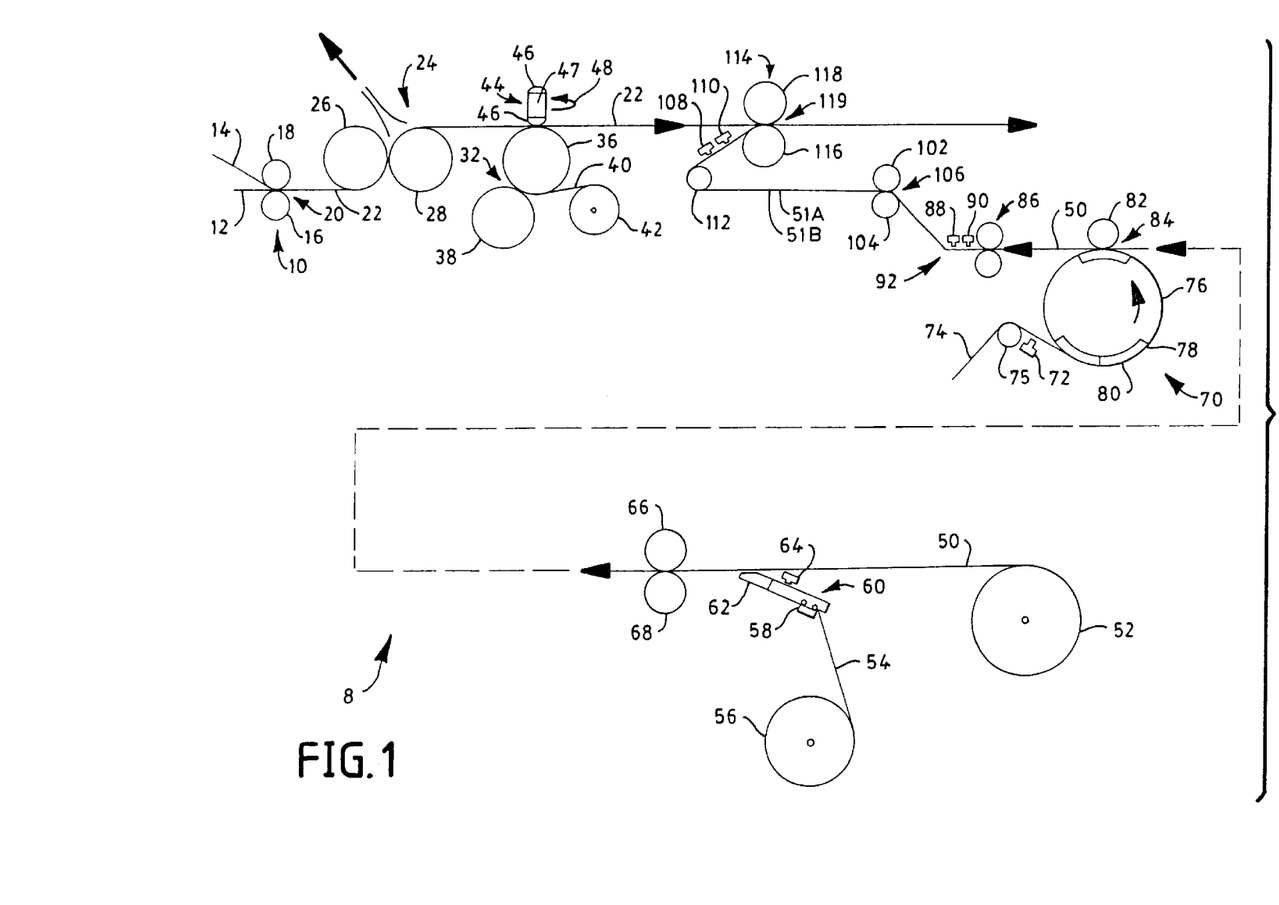
FIG. 1 shows a representative side elevation of apparatus for making absorbent articles of the invention.
Figure 9:
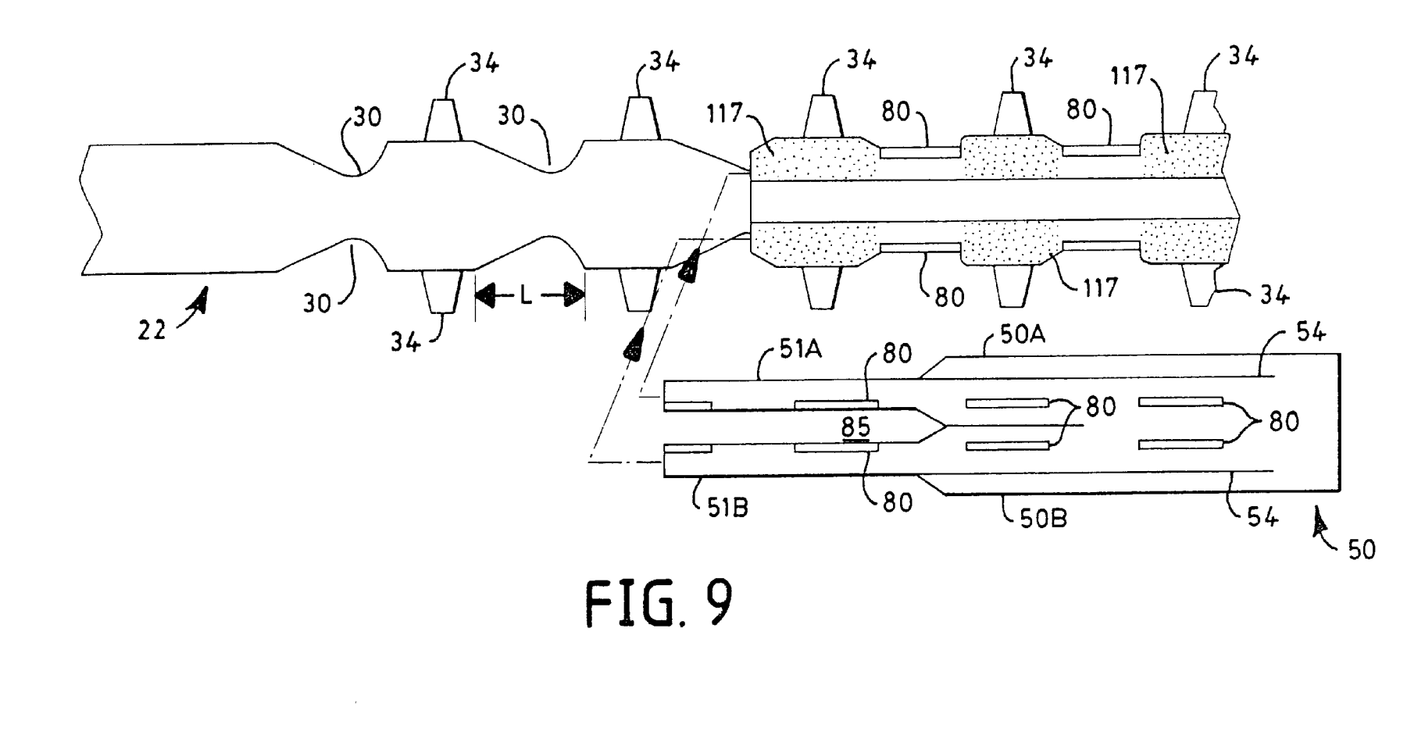
FIG. 9 shows a representative top view of the composite substrates being applied to the web sausage.

FIG. 1 shows an assembly system 8 for forming absorbent articles. System 8 includes a compression nip device 10 that secures a bodyside liner 12 and an absorbent core 13 (shown in FIGS. 10 and 11) to an outer cover 14. Compression nip device 10 comprises first and second rolls 16, 18 forming a first nip 20. First nip 20 applies pressure to the bodyside liner 12, outer cover 14, and absorbent core 13 therebetween, to form an absorbent article web sausage 22. Absorbent article web sausage 22 then moves to die cutter 24. Die cutter 24 includes an anvil roll 26 and a knife roll 28. Die cutter 24 cuts leg cut-outs 30 from web sausage 22 as shown in FIG. 9. Web sausage 22 proceeds to ear applicator 32. Ear applicator 32 secures ears 34, shown in FIG. 9, to web sausage 22 for mounting absorbent article 35 to a user. Ear applicator 32 includes a vacuum transfer roll 36 which supports ears 34 and a knife roll 38. Knife roll 38 cuts ears 34 from ear material 40 fed from supply roll 42. An elliptical rotary anvil 44 with pucks 46 intermittently forms a nip with transfer roll 36 to secure ears 34 on web sausage 22. Rotary anvil 44 rotates in a counterclockwise direction shown by arrow 48 whereby pucks 46 are moving in the same direction as web sausage 22 when the pucks interact with the web sausage.

Meanwhile, a substrate 50 of continuous web material is drawn from a supply roll 52. One or more elastomeric elements 54 are drawn from one or more elastomeric element supply rolls 56. The elastomeric elements 54 pass through thread guides 58 of guide apparatus 60. Guide fingers 62 guide elastomeric elements 54 toward substrate 50. Glue gun 64 applies adhesive to elastomeric elements 54. Elastomeric elements 54 preferably extend longitudinally along the length of the substrate at substantially equal distances from central axis 87 shown in FIGS. 2 and 3. Anvil rolls 66, 68 ensure securement of elastomeric elements 54 to substrate 50 by applying pressure to the elastomeric elements and the substrate.

Figure 2:
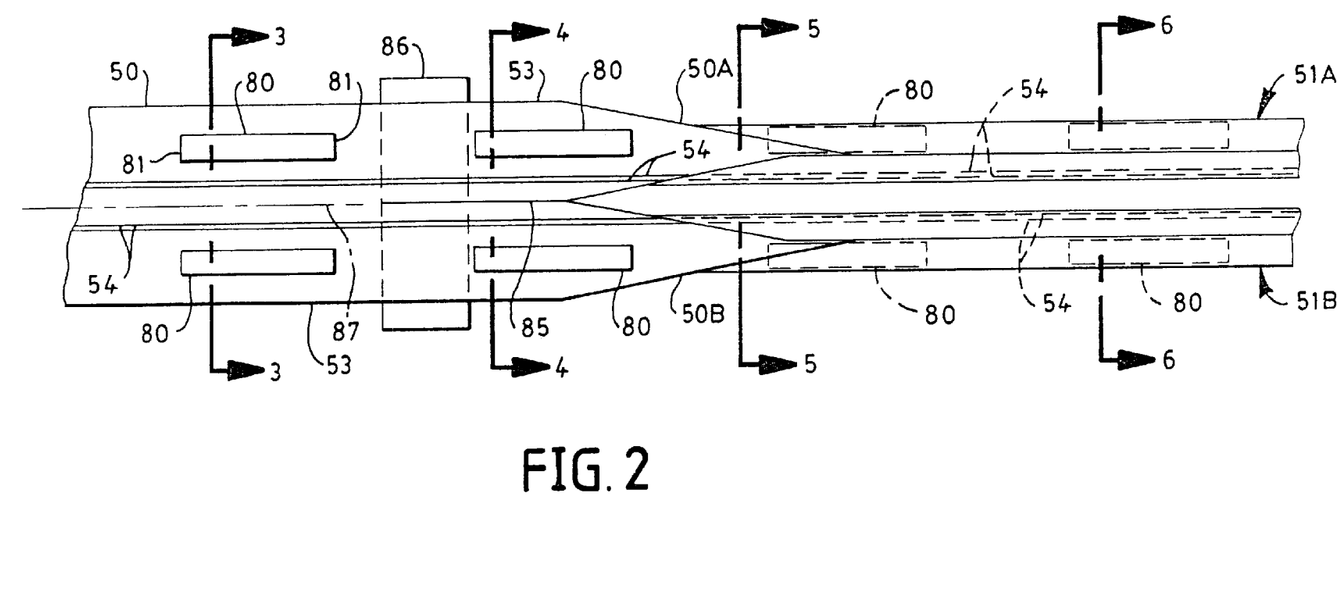
FIG. 2 shows a top view of a continuous containment flap substrate that supports elastomeric elements and spaced leg cuff pieces.
Figure 3:
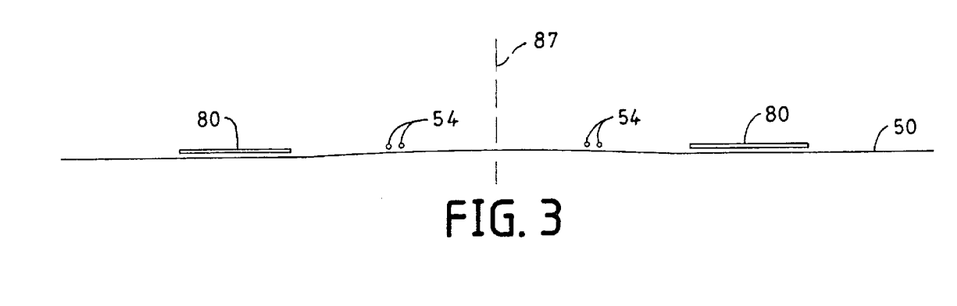
FIG. 3 shows a cross-sectional view of the substrate, elastomeric elements, and leg cuff pieces, and is taken at 3—3 of FIG. 2.

Substrate 50 then moves to leg cuff piece applicator 70. Preferably substrate 50 travels a substantially straight line path from supply roll 52 through anvil rolls 66, 68 to leg cuff piece applicator 70. Leg cuff piece applicator 70 includes a glue gun 72 that applies glue to leg cuff material 74. Pre-wrap roll 75 helps pre-feed/pre-wrap a variable velocity vacuum transfer roll 76. Variable velocity vacuum transfer roll 76 includes pucks 78 that support leg cuff pieces 80, and an anvil roll 82 forms a second nip 84 with vacuum roll 76. A hot knife (not shown) on vacuum transfer roll 76 cuts extensible leg cuff pieces 80 to a size preferably greater than the length "L" of the opening at leg cut-outs 30 shown in FIG. 9. Leg cuff piece applicator 70 then secures leg cuff pieces 80 to substrate 50 at transversely and longitudinally spaced locations as shown in FIGS. 2 and 3. A full description of vacuum transfer roll 76, as well as vacuum transfer roll 36, is set forth in patent application Ser. No. 08/381,362 titled "Method and Apparatus for Placing Discrete Parts onto a Moving Web" by Rajala et al, filed Jan. 31, 1995 and hereby incorporated by reference in its entirety.

Figure 4:
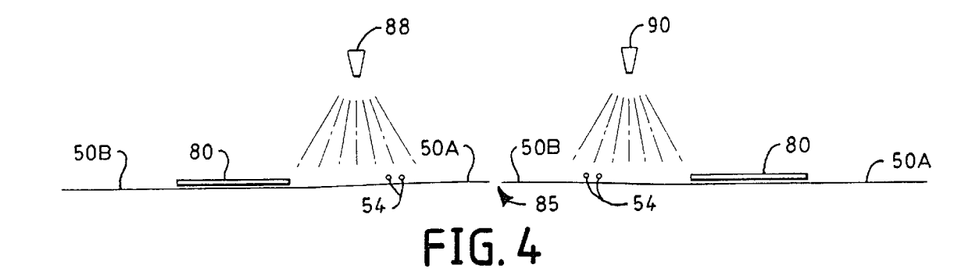
FIG. 4 shows a cross-sectional view of the substrate, elastomeric elements, and leg cuff pieces, and is taken at 4—4 of FIG. 2.

Cutting wheel 86 cuts or slits substrate 50 into two substrate portions 50A, 50B as shown in FIG. 2, forming slit 85 along the length of substrate 50. Glue guns 88, 90 then apply adhesive to substrate portions 50A, 50B as shown in FIG. 4.

Figure 6A:
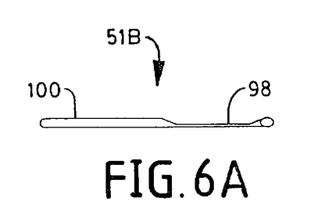
FIGS. 6A and 6B show a cross-sectional view of the composite containment flap substrates formed by folding of the substrate portions, and is taken at 6—6 of FIG. 2.
Figure 6B:
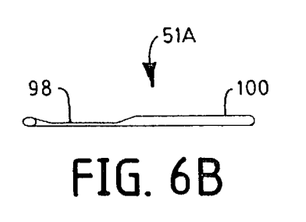

Folding mechanism 92, represented by an angle having arms aligned with the direction of movement of substrate 50 in FIG. 1, then folds both inside and outside portions of substrates 50A, 50B forming composite containment flap substrates 51A, 51B. Each composite containment flap substrate comprises an integral combination of a containment flap 98 and leg cuff 100 as shown in FIGS. 6A and 6B.

Next, anvil rolls 102, 104 apply pressure at nip 106 ensuring that the combination containment flaps 98/leg cuffs 100 of composite substrates 51A, 51B are property bonded by the adhesive and shaped to the desired folded configuration. Glue guns 108, 110 apply adhesive to respective composite substrates 51A, 51B near turning roll 112. Turning roll 112 turns respective composite substrates 51A, 51B toward web sausage 22 for securement thereto. Ultrasonic bonder 114 then bonds the composite substrates 51A, 51B comprising leg cuffs 100 and containment flaps 98 to web sausage 22, and finishes the edges of the respective composite substrates. Ultrasonic bonder 114 includes first and second bonding units, each unit including an ultrasonic rotary anvil roll 116 and a rotary ultrasonic horn 118 forming a respective nip 119.

Bodyside liner 12 may be manufactured from a wide selection of web materials, such as porous foams, reticulated foams, apertured plastic films or natural fibers. For example, bodyside liner 12 may comprise wood or cotton fibers. Other possible materials are synthetic fibers, such as polyester or polypropylene fibers, or a combination of natural and synthetic fibers. Bodyside liner 12 is suitably utilized to help isolate, from the wearer's skin, the liquids held in absorbent core 13.

Various woven and nonwoven fabrics can be used for bodyside liner 12. For example, bodyside liner 12 may be composed of a meltblown or spunbonded web of pofyolefin fibers. Bodyside liner 12 may also comprise a carded and/or bonded web composed of natural and/or synthetic fibers. Bodyside liner 12 may also be composed of a substantially hydrophobic material wherein the hydrophobic material is treated with a surfactant or otherwise processed to impart a desired level of wettability and hydrophilicity.

In a particular embodiment of the present invention, bodyside liner 12 may comprise a spunbonded polypropylene fabric composed of about 2.8–3.2 denier fibers formed into a web having a basis weight of about 22 grams per square meter and a density of about 0.06 grams per cubic centimeter. A preferred fabric is treated with about 0.3 weight percent of a surfactant Bodyside liner 12 can be formed from a single layer, or may comprise a multiplicity of components, layers, or partial layers, which correspond to any of the materials disclosed herein, as well as others known in the art.

Absorbent core 13 suitably comprises a matrix of hydrophilic fibers, such as a web of cellulosic fluff, preferably in combination with a high-absorbency material commonly known as superabsorbent material. In a particular embodiment, absorbent core 13 comprises a mixture of superabsorbent hydrogel-forming particles and wood pulp fluff. In place of the wood pulp fluff, one may use synthetic, polymeric, meltblown fibers or a combination of meltblown fibers and natural fibers. The superabsorbent material may be substantially homogeneously mixed with the hydrophilic fibers or may be otherwise combined into the absorbent care.

Alternatively, absorbent core 13 may comprise a laminate of fibrous webs and superabsorbent material or other suitable means of maintaining a superabsorbent material in a localized area.

Absorbent core 13 can have any of a number of shapes. For example, the absorbent core may be rectangular, T-shaped or I-shaped. It is generally preferred that absorbent core 13 be narrower in the crotch portion than in the rear and/or front portions. Absorbent core 13 generally does not extend over the entire dimensions of outer cover 14 or bodyside liner 12.

The superabsorbent material in absorbent core 13 can be selected from among natural, synthetic and modified natural polymers and materials. The high absorbency materials can be inorganic materials, such as silica gels, or organic compounds, such as crosslinked polymers. The term crosslinked refers to any means for effectively rendering normally water-soluble materials substantially water insoluble but swellable, whereby absorbent properties are available but the swelled material is substantially immobile after absorbing water-based liquids. Such means can include, for example, physical entanglement, crystalline domains, covalent bonds, ionic complexes and associations, hydrophilic associations such as hydrogen bonding, and hydrophobic associations or Van der Waals forces.

Outer cover 14 can be formed from a single layer, or from multiple components, layers, or partial layers, of material, such that the resulting outer cover is substantially impermeable to liquids. A typical outer cover 14 may be manufactured from a thin plastic film or other flexible liquid-impermeable material. For example, outer cover 14 can be formed from a polyethylene film having a thickness of from about 0.012 millimeters to about 0.051 millimeters. When it is desirable that the outer cover 14 have a more clothlike feeling, it may comprise a polyethylene film laminated to a surface of a nonwoven web, such as a spunbonded web of polyolefin fibers. For example, a polyethylene film having a thickness of about 0.015 millimeters may have thermally or otherwise laminated thereto a spunbonded web of polyolefin fibers having a thickness from 1.5 to 2.5 denier per filament, which nonwoven web has a basis weight of about 24 grams per square meter. Further, outer cover 14 can be formed of a woven or nonwoven fibrous web which has been totally or partially constructed or treated to impart a desired level of liquid impermeability to selected regions that are adjacent or proximate the absorbent core 13. Still further, outer cover 14 may optionally be composed of a micro-porous material which permits vapors to escape from absorbent core 13 and through outer cover 14 while preventing liquid exudates from passing through the outer cover.

Ears 34 preferably comprise mechanical fasteners such as hooks of a hock and loop fastening system, and are preferably mounted on outer cover 14. Cooperative attachment loop material or other fastener surface is provided at e.g. the outer surface (not shown) of outer cover 14 on e.g. the front portion of the respective absorbent articles 35. The exemplary loop material is adapted to releasably engage with hook material on the respective ear. Other well known fastening systems can also be used to support absorbent article 35 on a user. For example, a cohesive system, an adhesive fastener system or the like may also be utilized to secure the absorbent article about the crotch and lower trunk portion of the user.

Operation of the absorbent article assembly system 8 is as follows. First and second anvil rolls 16, 18 of compression nip device 10 form first nip 20. At least one of the rolls is driven by a drive (not shown). Rolls 16, 18 press continuous webs of bodyside liner 12 and outer cover 14 against each other at nip 20, trapping spaced elements of absorbent core 13 therebetween, thereby securing bodyside liner 12, absorbent core 13 and outer cover 14 to one another at nip 20, preferably by gluing. These three elements, when secured to each other, mutually form absorbent article web sausage 22, with spaced elements of absorbent core 13 being disposed between bodyside liner 12 and outer cover 14. Other known devices can also be utilized to form web sausage 22.

Bodyside liner 12 and outer cover 14 preferably have substantially the same dimensions. The webs of bodyside liner 12 and outer cover 14 are preferably aligned so their outer edges are substantially aligned with and contact one another when web sausage 22 is formed. The so joined webs of bodyside liner 12, outer cover 14, and the spaced elements of absorbent core 13 comprise precursors of respective serially aligned absorbent articles 35 along the length of web sausage 22. As indicated in the drawings, web sausage 22 comprises a continuous web sausage.

After leaving nip 20, web sausage 22 then enters die cutter 24 which cuts leg cut-outs 30. The cutting is done by knife roll 28 in combination with anvil roll 26. Knife roll 28 has knives (not shown) arranged in a pattern consistent with making leg cut-cuts 30 illustrated in FIG. 9. Preferably both leg cut-outs 30 on a given absorbent article precursor are made simultaneously by spaced knives (not shown). Absorbent core 13, preferably is not contacted by any of the knives of die cutter 24. Preferably, none of the layers forming web sausage 22 contain elastomeric material.

As used herein, "elastomeric material" means material which can be stretched about 50% to about 450% in one direction, and which will return to approximately its original dimensions when released. Preferably all of the material removed by die cutter 24 comprises non-elastomeric material.

Ear applicator 32 cuts, and thereby creates, ears 34 from an incoming web of ear material 40 drawn from supply roll 42, and transfers the ears to web sausage 22. Knife roll 38 rotates with vacuum transfer roll 36, cutting ear material 40 to create the ears. Elliptical rotary anvil 44 rotates about central axis 47 as shown by arrow 48 in FIG. 1. Rubber pucks 46 on rotary anvil 44 intermittently form a nip with transfer roll 36 and thereby assist in securing ears 34 to web sausage 22. After an ear 34 is secured, the respective rubber puck 46 rotates out of contact with web sausage 22. The opposing puck 46 then rotates into such contact, to mount another ear 34 when rotary anvil 44 has rotated about 180 degrees. Such process is repeated by continuing rotation of rotary anvil 44 and transfer roll 36. The ears can be secured to web sausage 22 by adhesive or other methods. Pucks (not shown) on vacuum transfer roll 36 rotate into contact with web sausage 22 for transferring ears 34 to the web sausage.

While compression nip device 10, die cutter 24, and ear applicator 32 are operating, substrate 50 comprising a continuous web material is being drawn from supply roll 52. Elastomeric element supply roll 56 supplies continuous threads of elastomeric elements 54 to guide apparatus 60. Guide apparatus 60 utilizes thread guides 58 and guide fingers 62 to place and secure elastomeric elements 54 to substrate 50.

Substrate 50 can comprise any of the materials mentioned as suitable for bodyside liner 12. Substrate 50 preferably comprises a soft nonwoven fabric material. Substrate 50 has a length dimension. Substrate 50 comprises a main body extending along the length dimension, and opposing outer edges 53.

Glue gun 64 applies adhesive to elastomeric elements 54 just before the elastomeric elements are secured to substrate 50. Elastomeric elements 54 are adhered at opposing inner locations spaced both from central axis 87 of substrate 50 as shown in FIG. 2 and from the opposing outer edges 53 of substrate 50. Central axis 87 runs the length of substrate 50 and is substantially centered in the substrate. Elastomeric elements 54 preferably continuously run the entire length of substrate 50 and preferably are spaced outwardly substantially equal distances from central axis 87, and inwardly substantially equal distances from the respective outer edges 53. Preferably, spaced leg cuff pieces 80, which will be described in more detail later, are spaced outwardly from elastomeric elements 54 as shown in FIG. 2. Substrate 50 then passes through anvil rolls 66, 68 which apply pressure to elastomeric elements 54 and substrate 50, ensuring securement of the elastomeric elements to the substrate.

Figure 5:
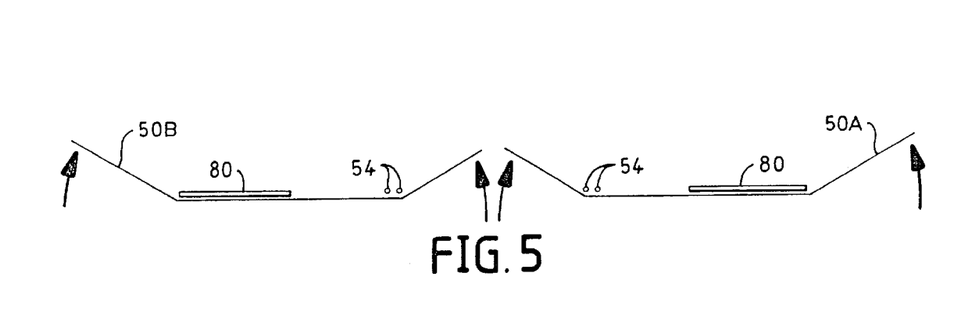
FIG. 5 shows a cross-sectional view of the substrate portions being folded, after separation, with elastomeric elements and leg cuffs thereon, and is taken at 5—5 of FIG. 2.

Any number of elastomeric elements 54 can be utilized in the invention. FIGS. 3–5 show a total of four elastomeric elements 54 applied to substrate 50. However, any number of elastomeric elements, preferably an even number, can be secured to the substrate. Elastomeric elements 54 can comprise strands, ribbons, or one or more layers of a polymeric and/or elastomeric material, such as a rubber material, which is adhered to substrate 50 in a stretched condition. A suitable elastomeric element can be composed of a 470 decitex LYCRA elastomer, a 620 decitex LYCRA elastomer or other elastomers with suitable characteristics. Elastomeric elements 54 create elastic tension for containment flaps 98 and therefore must be of appropriate strength and size.

While continuous elastomeric elements 54 intermittently glued to substrate 50 are the preferred embodiment, the elastomeric elements can be discontinuous, having a length substantially the same as leg cuff pieces 80 shown in FIG. 2. In such an embodiment, elastomeric elements 54 can be attached to substrate 50 in a manner similar to leg cuff pieces 80. FIG. 3 shows one embodiment of the invention in cross-section, including two spaced pairs of elastomeric elements 54 about which containment flaps 98 are folded.

Glue gun 64 can comprise a single glue gun with multiple ports, or a plurality of individual glue guns for each elastomeric element 54 being secured to substrate 50. Glue guns 64 preferably operate in a timed or registered manner to intermittently glue elastomeric elements 54 to substrate 50. While FIG. 1 shows glue gun 64 applying adhesive to elastomeric elements 54, adhesive can instead be applied directly to substrate 50 at locations where guide apparatus 60 places elastomeric elements on the substrate, or can be applied to both substrate 50 and elements 54. The glued portions of elastomeric elements 54 preferably extend approximately the same length as leg cuff pieces 80 and preferably along the same length of substrate 50 as the leg cuff pieces in registration with leg cuff pieces 80; but elastomeric elements 54 preferably are spaced inwardly from leg cuff pieces 80 when both are applied to substrate 50.

While gluing is the preferred method of attaching elastomeric elements 54 to substrate 50, other known methods, such as melt bonding or heat bonding can also be utilized.

Substrate 50 moves from guide apparatus 60 through the nip formed by rolls 66, 68, then to leg cuff piece applicator 70. The dashed line in FIG. 1 indicates that the elastomeric guide apparatus 60 can be in line with leg cuff piece applicator 70, and is placed underneath apparatus 60 merely for purposes of illustration.

Leg cuff piece applicator 70 applies pairs of opposed spaced leg cuff pieces 80 to substrate 50 using variable velocity vacuum transfer roll 76 having pucks 78 that support leg cuffs 80, representatively illustrated in FIG. 1. Glue gun 72 supplies adhesive to a continuous web of leg cuff material 74.

In an alternative embodiment (not shown), glue gun 72 is positioned adjacent substrate 50. Glue gun 72 is timed or registered to intermittently apply adhesive to opposed spaced portions of substrate 50 and along a length of substrate 50 therebetween. Leg cuff pieces 80 are brought adjacent substrate 50 of the leg cuff pieces with the ends 81 and one side of each leg cuff 80 in registration with the adhesive on substrate 50, and are secured to the substrate.

Pre-wrap roll 75 helps pre-feed/pre-wrap vacuum transfer roll 76 and maintain leg cuff material 74 in continuous contact with vacuum transfer roll 76 before, during and after cutting of the leg cuff material. The variable rotational velocity of vacuum transfer roll 76 is controlled to operate at a first rotational velocity whereby the speed of a segment of the roll substantially equals the speed of leg cuff material 74 when receiving a length of the leg cuff material onto the segment of the roll. The continuous web of leg cuff material 74 is then cut into individual leg cuff pieces 80 by a hot knife (not shown) on vacuum transfer roll 76, and is supported by vacuum on vacuum transfer roll 76.

When leg cuffs are to be applied to substrate 50, the rotational velocity of the respective segment is changed such that the speed of the segment substantially equals the speed of substrate 50. By matching the surface speed of the segment to the speed of substrate 50, proper transfer is effected. Variable velocity vacuum roll 76 applies leg cuff pieces 80, such as by adhesive pressure, to substrate 50 with assistance of roll 82.

Individual extensible leg cuff pieces 80, at least when extended, have a length longer than the length of leg cut-outs 30. Prior to securement to substrate 50, leg cuff pieces 80 preferably are extended to a dimension representing about 5% to about 95% of their stretch-to-stop elongation, and most preferably 20% to 50% of their stretch-to-stop elongation. Leg cuff pieces 80 are secured to substrate 50 in such partially stretched condition, with substrate 50 extended preferably to its stretch-to-stop limit. At minimum, the percent elongation of leg cuff piece 80 at securement to substrate 50 is greater than the percent elongation of substrate 50. Accordingly, leg cuff pieces 80 provide a degree of retraction properties different from, preferably greater than, the retraction properties of substrate 50. FIG. 3, taken at 3—3 in FIG. 2, shows the preferred spacing of leg cuff pieces 80 on substrate 50 on opposing sides of elastomeric elements 54. Leg cuff pieces 80 are at spaced opposing locations with respect to each other along substantially the same length of web substrate 50.

Web material 74 used to make leg cuff pieces 80 can comprise, for example, a laminate including first and second outer nonwoven facing layers on opposing sides of an elastomeric core layer, the elastomeric core layer comprising a thermoplastic elastomeric composition such as a styrene ethylene butylene styrene terpolymer. Extensible leg cuff pieces 80 can also comprise a plurality of elastomeric elements comprising strands, ribbons or the like secured in a stretched condition to a nonelastomeric piece of material, the elastomeric elements extending along the length of the nonelastomeric piece of material. Leg cuff pieces 80, as shown, are discontinuous structures comprising elastomeric material.

Examples of other materials of which all or portions of leg cuff pieces 80 may be comprised include, without limitation, spandex/nonwoven laminated webs, extruded elastomeric webs or meltblown webs, cross-machine direction stretchable web materials made with stretchable nonwovens, stretchable foam webs and the like.

From leg cuff piece applicator 70, substrate 50 moves to cutting wheel 86. Cutting wheel 86 includes a knife or blade (not shown) which slits substrate 50 along its length into two substrate portions 50A. 50B as shown at dashed central axis 87 in FIG. 3. A slit 85, formed by cutting wheel 86, is shown in FIG. 9. While cutting wheel 86 is disclosed, the invention contemplates other well known elements performing the same cutting function. For example, a tension bar having a stationary or moving blade mounted at a proper angle with respect to substrate 50 can slit the substrate along its length.

Folding mechanism 92 is represented by an angle or bend in substrate portions 50A, 50B of substrate 50 in FIG. 1. Folding mechanism 92 folds substrate portions 50A, 50B to form composite substrates 51A, 51B. Folding mechanism 92 comprises a well known apparatus that folds webs or substrates. Such a folding apparatus is shown in U.S. Pat. No. 4,900,384, issued Feb. 13, 1990 to Sanders et al and herein incorporated by reference. Other similar folding mechanisms are well known in the art and can be utilized with assembly system 8.

Glue guns 88, 90 apply adhesive to substrate portions 50A and 50B respectively, as shown in FIG. 4. Folding mechanism 92 then folds substrate portions 50A, 50B along the continuous length thereof as shown in FIG. 5 securing the outside edges to facing portions of the main body. When folding is completed, composite substrates 51A, 51B are formed. Each integrated continuously folded composite substrate 51A, 51B comprises a leg cuff 100 integral with a containment flap 98 as shown in FIGS. 6A, 6B. Driven anvil rolls 102, 104, forming nip 106, then compress composite substrates 51A, 51B to ensure securement of the adhesive, to thereby secure the folds.

Figure 7A:
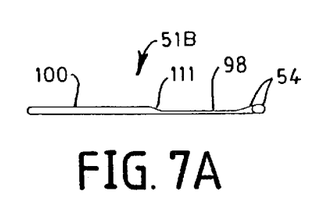
FIGS. 7A and 7B show a cross-sectional view of composite substrates of FIGS. 6A and 6B, with adhesive applied thereto.
Figure 7B:
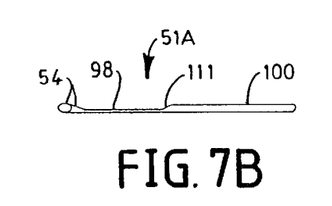

Turning roll 112 then turns composite substrates 51A, 51B toward ultrasonic bonder 114. Glue guns 108, 110 apply adhesive 111 to composite substrates 51A, 51B, preferably as lines of adhesive at a central location along the length of each composite substrate, as shown in FIGS. 7A and 7B. The integral leg cuffs 100 and containment flaps 98 of integral folded composite substrates 51A, 51B are then moved into position below web sausage 22 as shown in the cross-sectional view of FIG. 8 and secured thereto. Of course, composite substrates 51A, 51B can, in the alternative, be placed above web sausage 22 or in any other spaced arrangement. Web sausage 22 is a representation of, for example, bodyside liner 12, absorbent core 13, outer cover 14 and any other element contained between bodyside liner 12 and outer cover 14.

Ultrasonic bonder 114 then finishes and smoothes the absorbent article. Ultrasonic bonder 114 includes anvil rolls 116 and rotary ultrasonic horns 118. Each rotary ultrasonic horn 118 is biased against a respective anvil roll 116. As web sausage 22 and composite substrates 51A, 51B pass, each rotary ultrasonic horn 118 vibrates, generating ultrasonic energy, preferably at a frequency of about 20 KHz. The ultrasonic energy finishes and smoothes raw edges of each, of the leg cuffs 100 and smoothes unevenness due to their elasticity and unregistered gluing. Each ultrasonic horn 118 is disposed over a different one of the lines of spaced leg cuffs 100 being secured to web sausage 22. A respective ultrasonic horn 118 typically has a pattern 117 of dots forming a quilted or other pattern or look. This quilted pattern 117 is formed by blending portions of composite substrates 51A, 51B into web sausage 22 with ultrasonic energy as shown in FIG. 9. This pattern prevents curl of leg cuffs 100 and/or containment flaps 98, caused by their elasticity and unregistered gluing, from altering the appearance, or the consistency of performance, of absorbent article 35. Thus, after the ultrasonic treatment, absorbent articles 35 have a smooth, finished look where composite substrates 51A, 51B are secured to web sausage 22.

While an ultrasonic bonder 114 is disclosed, other well known devices can be utilized to join composite substrates 51A, 51B to web sausage 22. For instance, ultrasonic bonder 114 can be replaced by a pair of anvil rolls forming a nip. The anvil rolls compress web sausage 22 against composite substrates 51A, 51B ensuring adhesive 111 secures the elements to each other.

Downstream of ultrasonic bonder 114, web sausage 22 is cut into a plurality of absorbent articles or workpieces. A cutting machine (not shown) severs web sausage 22 transversely across its width. The cutting machine is timed or registered to sever web sausage 22 at locations spaced along the length of the web sausage, and substantially centered between longitudinally spaced leg cuffs 80. The cutting machine also severs elastomeric elements 54, if they have not already been severed earlier in the process.

Severing of web sausage 22 is done by any of a variety of well known cutting machines. For example, a final cut-off roll (not shown) having a knife (not shown) extending across the roll, in combination with an anvil roll (not shown) severs web sausage 22. There is preferably a gap about 0.25 inch wide between the cut-off roll and the anvil roll (not shown). The absorbent articles severed from web sausage 22 are transferred by conveyor to a stacker (not shown).

Figure 10:
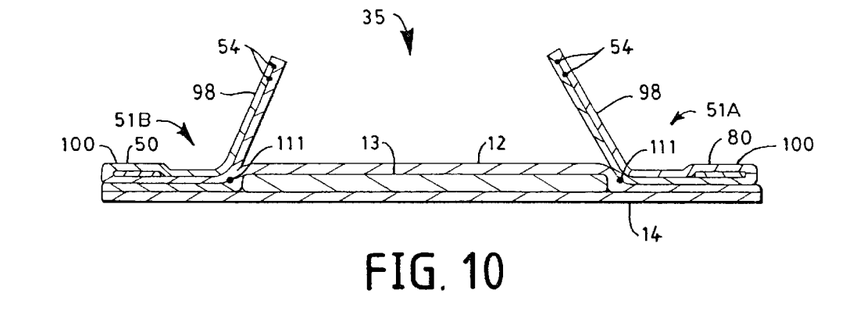
FIG. 10 shows a cross-sectional view of a first embodiment of absorbent articles formed by apparatus and methods of the invention.

In the embodiment shown in FIGS. 7A and 7B, adhesive 111 is placed as a continuous line of adhesive between containment flap 98 and leg cuff 100. This embodiment forms a "V-cuff" type absorbent article 35 as shown in FIG. 10. Absorbent article 35 includes absorbent core 13, bodyside liner 12 and outer cover 14. Leg cuffs 100 extend outwardly from absorbent core 13, along bodyside liner 12 and outer cover 14, and containment flaps 98 extend upwardly at an angle from the general structure formed by absorbent core 13, bodyside liner 12 and outer cover 14.

Figure 8:
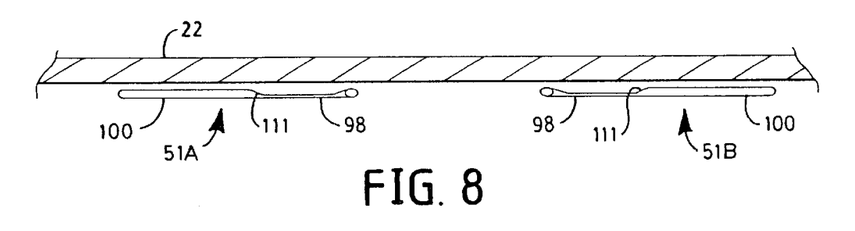
FIG. 8 shows a cross-sectional view showing the composite substrates applied to the web sausage.
Figure 11:
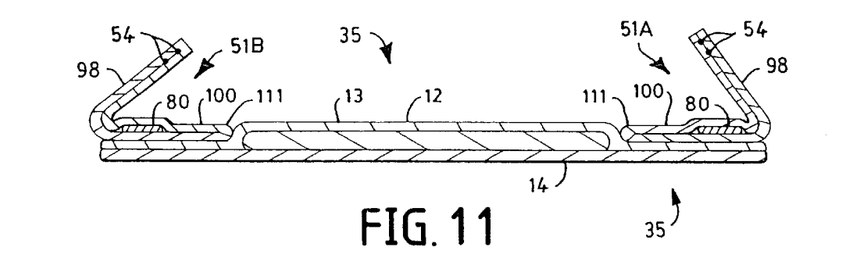
FIG. 11 shows a cross-sectional view of a second embodiment of absorbent articles formed by apparatus and methods of the invention.

FIG. 11 shows another embodiment where adhesive is applied as a continuous line of adhesive along the outside edge of leg cuff 100, as compared to FIG. 8. Leg cuff 100 glues to web sausage 22 and extends outwardly therefrom. Containment flap 98 is folded inwardly to contact a users body and contain exudates. Folding can be accomplished by a folding device, as described earlier, or any other conventional folding apparatus. An ultrasonic bonder (not shown) can ensure the fold remains in place by bonding the outward folded edge of the flap. The embodiment of FIG. 11 generally comprises a "C-cuff" type absorbent article 35 having leg cuffs formed in a C-shaped structure as illustrated in FIG. 11.

While FIG. 1 shows glue guns 108, 110 applying adhesive to composite substrates 51A, 51B, the glue can be applied directly to web sausage 22 at locations that will contact selected parts of composite substrates 51A, 51B. Once again, the adhesive preferably comprises a continuous line of glue along the length of web sausage 22.

While FIG. 1 shows ear applicator 32 applying ears 34 to web sausage 22 before applying substrate portions 50A, 50B to the web sausage, the order can be reversed and ear applicator 32 can follow ultrasonic bonder 114. Further, the order of other work stations, such as guide apparatus 60 which applies elastomeric elements 54 and leg cuff piece applicator 70, can be changed.

Base Structure Embodiment

Figure 12:
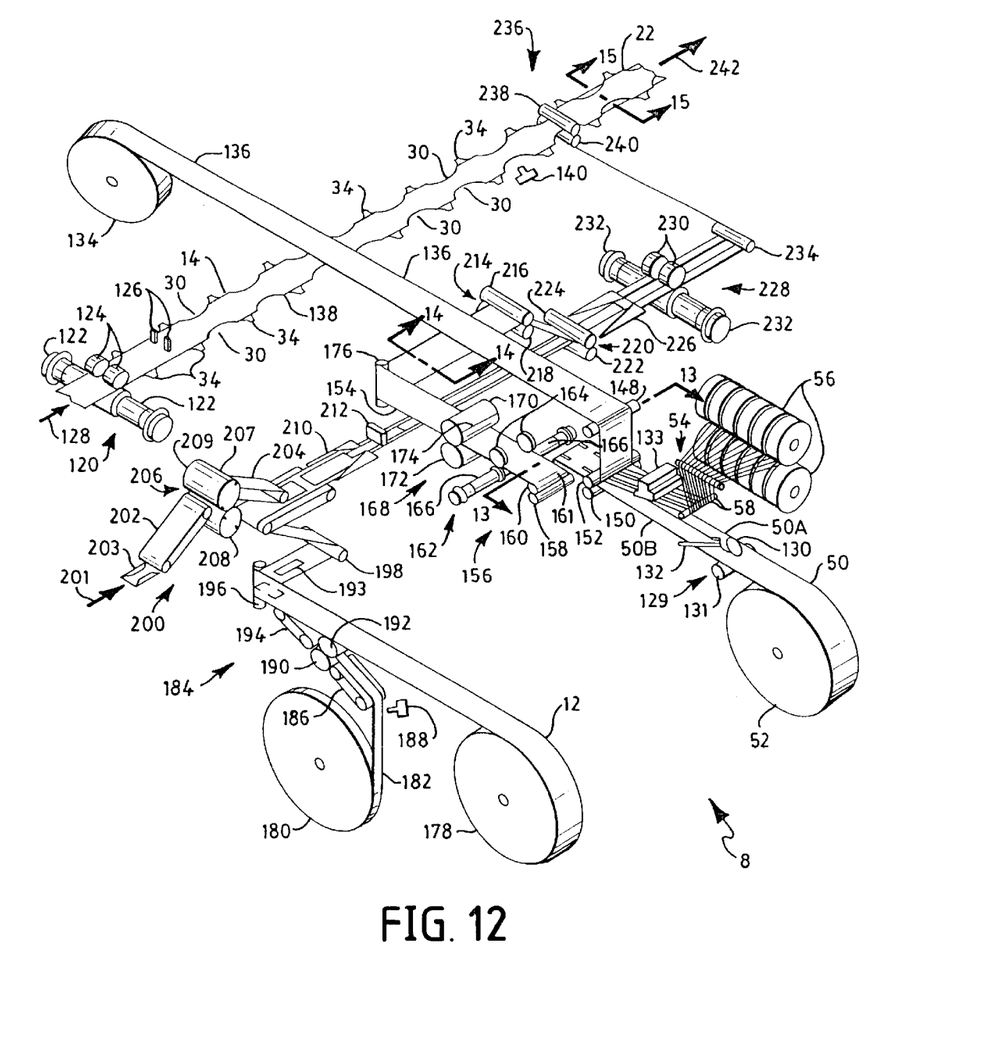
FIG. 12 shows a representative pictorial view of a second embodiment of apparatus used in the invention.

FIG. 12 shows another embodiment of absorbent article assembly system 8 that forms containment flaps 98 and leg cuffs 100 on a single workpiece. The workpiece supports bodyside liner 12 and outer cover 14. Ear piece bonding device 120 comprises ultrasonic horns 122 and anvil rolls 124 that intermittently bond ears 34 to outer cover 14. Leg cut-out devices 126 sever leg cut-cuts 30 from outer cover 14 which moves in a direction shown by arrow 128.

Elsewhere, first substrate 50 is fed from supply roll 52. A cutting device 129 including a cutting wheel 130 and a bottom roll 131 having a shoulder, slit substrate 50 into two substrate portions 50A, 50B. A Z-bar 132 spreads or spaces substrate portions apart from one another. Elastomeric supply rolls 56 supply elastomeric elements 54 through thread guides 58 to substrate portions 50A, 50B. Intermittent glue gun 133 applies adhesive to elastomeric elements 54 to secure the elements to respective substrate portions 50A, 50B.

In the meantime, a second base roll 134 unrolls a second substrate 136, preferably comprising a polyethylene material. Turning roll 148 turns second substrate 136 downwardly toward first substrate 50. Then second substrate 136 and first substrate 50 are joined by a pair of rolls 150, 152 forming a nip. First substrate 50 and second substrate 136 together form a base structure 154 having elastomeric elements 54 therebetween. Base structure 154 proceeds to J-fold device 156 including anvil rolls 158, 160. J-fold device 156 includes folding board 161 that folds the outside edges of base structure 154 inwardly and upwardly to form ends of containment flaps 98. J-fold bonder 162, comprising anvil rolls 164 and ultrasonic horns 166, then bonds or strengthens the J-folded edges of base structure 154. Base structure 154 then moves to elastomeric element cutter 168. Elastomeric element cutter 168 comprises a cutter roll 170 and an anvil roll 172. When cutter element 174 of cutter roll 170 contacts base structure 154 in a nip formed between rolls 170, 172, elastomeric elements 54 are crushed, and thereby severed. Turning roll 176 turns the direction of travel of base structure 154.

Elsewhere, bodyside liner supply roll 178 supplies a continuous web of bodyside liner material 12. Surge layer supply roll 180 supplies surge layer material 182. Surge layer 182 enters surge layer applicator 184 where the surge layer is cut and applied at spaced locations along the web of bodyside liner material 12. Surge layer applicator 184 includes a first conveyor 186 that receives surge layer material 182. A glue gun 188 applies adhesive to surge layer 182 while the layer is traversing first conveyor 186. A knife roll 190 and a rotary anvil 192 form a nip. When a transverse cutting blade (not shown) on knife roll 190 contacts surge layer 182, the surge layer is severed. Then a second faster separating conveyor 194 receives the severed segment 193 of surge layer 182 and advances the segment to bodyside liner 12. Surge layer segment 193 is secured to bodyside liner 12 by the adhesive from glue gun 188. Bodyside liner 12, with surge layer segment 193 secured thereto, then follows a pair of turning rolls 196, 198 to absorbent core applicator 200.

Arrow 201 shows the direction absorbent core material (not shown) travels to reach absorbent core applicator 200. Absorbent core applicator 200 places absorbent core 13 over bodyside liner 12 and surge layer 182.

Absorbent core applicator 200 includes a first conveyor 202 operating at a first speed and a second conveyor 204 operating at a second faster speed. Absorbent core applicator 200 includes a pad cut-off device 206 comprising an anvil roll 208 and a knife roll 209. Pad cut-off device 206 severs an absorbent core 13 from a length of absorbent core material 203 and absorbent core 13 is transferred to folding device 210.

Folding device 210 folds a portion of bodyside liner 12 around absorbent core 13. Glue gun 212 applies adhesive to bodyside liner 12.

Base structure 154 tranverses a first fast nip 214 formed by anvil rolls 216, 218. Then base structure 154 advances so a second nip 220, formed by rolls 222, 224, which rolls 222, 224 are rotating slower than first nip 214. Second nip 220 joins base structure 154 to bodyside liner 12 supporting absorbent core 13. Folding device 226 then folds containment flaps 98, formed in base structure 154, inwardly and downwardly around absorbent core 13. Ultrasonic bonder 228 comprising anvil rolls 230 and ultrasonic horns 232 then bonds or secures containment flaps 98 of base structure 154 in an inwardly folded downward direction. Folding device 226, as well as folding device 210 mentioned earlier, can comprise the folding apparatus of U.S. Pat. No. 4,900,384, or other folding mechanisms well known in the art.

Base structure 154 turns on turning roll 234 to join outer cover 14 having leg cut-outs 30 and ears 34 at compression nip device 236. Glue gun 140 applies adhesive to outer cover 14. Compression nip device 236 including anvil rolls 238, 240 secures outer cover 14 to the combination of bodyside liner 12 and base structure 154 forming web sausage 22. Web sausage 22 then moves to other work stations along a path shown by arrow 242.

In operation, ear piece bonding device 120 secures ears 34 to outer cover 14. Ears on outer cover 14 enter along a path shown by arrow 128. Separate ultrasonic horns 122, in combination with rotary anvil rolls 124, bond opposing ears spaced outwardly on outer cover 14. Ultrasonic horns 122, preferably operate at 20 KHz.

While an ultrasonic bonding device is disclosed, other known securing methods, such as adhesive bonding of ears 34 to outer cover 14 can be utilized. Furthermore, ears 34 can be attached to outer cover 14 or web sausage 22 later in the process.

Leg cut-out devices 126 then create leg cut-outs 30 in outer cover 14. The cutting loci of the respective leg cut-out devices effectively move inwardly and outwardly while outer cover 14 passes underneath to form the shape of leg cut-outs 30. A variety of known cutter devices are acceptable for leg cut—cut devices 126.

Elsewhere in absorbent article assembly system a, first substrate 50 is fed from supply roll 52. Substrate 50 preferably comprises a spunbond, non-woven material. However, substrate 50 can comprise any of the materials described earlier for bodyside liner 12.

Cutting device 129 slits substrate 50 along its length into two substrate portions 50A, 50B having substantially the same width. Cutting device 129 includes a rotating blade wheel 130 centered on substrate 50. Substrate portions 50A, 50B are spread apart by Z-bar 132 into a pair of spaced webs having approximately the same width. Z-bar comprises a pair of outwardly angled arms that space apart substrate portions 50A, 50B. The spacing of substrate portions 50A, 50B reduces the amount of material used in the manufacturing process, and thereby decreases the cost of the absorbent articles 35 being manufactured. Preferred spacing between substrate portions 50A, 50B is about 3 to 4 inches.

As substrate portions 50A, 50B advance, elastomeric elements 54 from elastomeric supply rolls 56 travel through thread guides 58 to substrate portions 50A, 50B. Glue gun 133 intermittently applies adhesive to elastomeric elements 54 and/or substrate portions 50A, 50B depending on the elements' relative positions.

Figure 13:
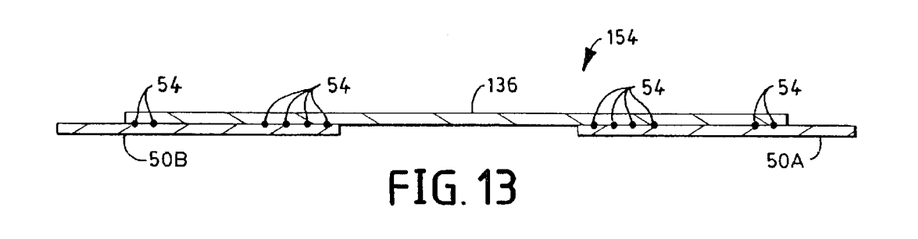
FIG. 13 shows a cross-sectional view of a base structure, and is taken at 13—13 of FIG. 12.

Meanwhile, second substrate 136 advances from a second base roll 134 toward direction changing roll 148 as shown in FIG. 12. When second substrate 136 meets first substrate portions 50A, 50B, at rotary anvil rolls 150, 152, the substrate and substrate portions are secured to one another. Adhesive from glue gun 133 and pressure between the rolls 150, 152 secure elastomeric elements 54 between first substrate portions 50A, 50B and second substrate 136, and secures first substrate portions 50A, 50B to second substrate 136 to form base structure 154 as shown in FIG. 13. Base structure 154 has a main body extending along a length dimension, opposing outside edge portions, and opposing outside edges 155 on the outside edge portions.

While second substrate 136 preferably comprises polyethylene material, it can also comprise the materials set forth earlier for outer cover 14 or bodyside liner 12. Substrate 136 preferably is impermeable to liquids.

Figure 14:
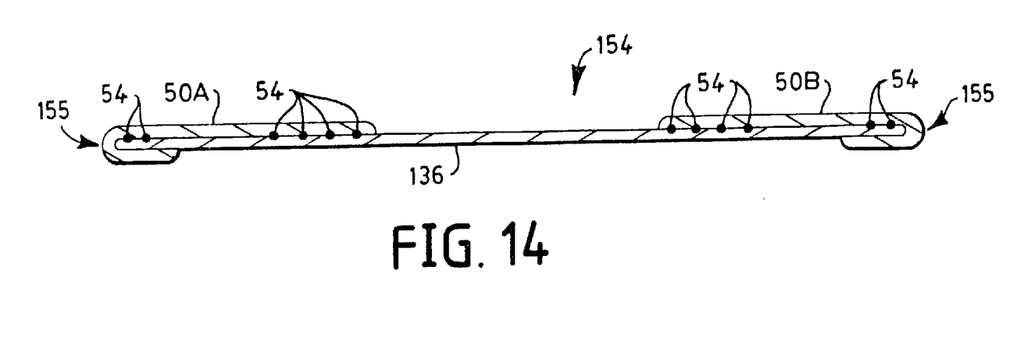
FIG. 14 shows a cross-sectional view of the J-folded base structure, and is taken at 14—14 of FIG. 12.

Base structure 154 then advances to J-fold device 156. Folding board 161 folds the ends of base structure 154 into substantially a J-shape as shown in FIG. 14. The J-folded base structure 154 advances to rotary anvil rolls 158, 160 forming a nip. The nip squeezes and compresses base structure 154 so the ends maintain their shapes.

Base structure 154 advances to J-fold ultrasonic bonder 162. J-fold ultrasonic bonder 162 includes ultrasonics horns 166 that vibrate at ultrasonic frequencies known to those skilled in the art. Rotary anvil rolls 164, combined with horns 166, form a nip. Ultrasonic energy applied to base structure 154 in the nip bonds the J-fold shape at the outside edges or creases of the base structure. The pair of ultrasonic horns 166 and anvil rolls 164 are spaced apart as shown in FIG. 12. Ultrasonic bonder 162 ensures the J-folded edges of base structure 154 maintain their shape shown in FIG. 14.

As base structure 154 advances, elastomeric element cutter 168 crushes or sufficiently weakens the elastomeric elements 54 inside the base structure so the elements snap or break without cutting or damaging either of substrates 50, 136. Elastomeric element cutter 168 includes a cutter roll 170 with a cutter element 174 and an anvil roll 172. Cutter element 174 passes transversely across base structure 154 upon rotation of cutter roll 170. When cutter element 174 contacts base structure 154, it applies a pressure great enough to crush elastomeric elements within the base structure. Cutter element 174 does not have an edge sharp enough to damage substrates 50, 136. The severing of elastomeric elements 54 occurs at approximately the top and back side edges of yet-to-be-formed absorbent articles 35. Turning roll 176 then turns base structure 154 toward a workstation that mounts absorbent core 13 and bodyside liner 12 to the base structure. FIG. 14, taken between turning roll 176 and fast nip 214, shows base structure 154 reversed or inverted from the position shown in FIG. 13 due to turning roll 176.

At another location in assembly system 8, bodyside liner supply roll 178 feeds bodyside liner 12 to surge layer applicator 184. Surge layer supply roll 180 supplies surge layer 182 to surge layer applicator 184. A first conveyor 186 operating at a first speed receives surge layer 182. Glue gun 188, depending on its position, applies adhesive to a first surface of surge layer 182 either before or after the layer is on the conveyor. First conveyor 186 feeds surge layer 182 to a cutting mechanism formed by knife roll 190 and rotary anvil roil 192. Knife roll 190 includes a knife (not shown) that severs surge layer 182 transverse to its direction of travel to create discrete surge layer segments 193. A detached surge layer segment 193 then passes to second conveyor 194 which operates at a greater speed than first conveyor 192. Second conveyor 194 spaces apart surge layer segments 193 for spaced attachment to bodyside liner 12 and for ultimate positioning adjacent absorbent core 13.

When the absorbent article 35 is in use on a consumer, the surge layer segment 193 spreads exudates across its entire surface to enhance the absorption of absorbent core 13. Surge layer segments 193 can be made of well known materials. Further, surge layer segments, and surge layer 182 can comprise materials set forth in U.S. patent application Ser. No. 206,986 by C. Ellis and D. Bishop, entitled, "Fibrous Nonwoven Web Surge Layer for Personal Care Absorbent Articles and the Like", filed Mar. 4, 1994; and U.S. patent application Ser. No. 206,069 by C. Ellis and R. Everett, entitled, "Improved Surge Management Fibrous Nonwoven Web for Personal Care Absorbent Articles and the Like", filed Mar. 4, 1994; the disclosures of which are herein incorporated by reference.

Bodyside liner 12, with a surge layer segment 193 thereon, then advances around turning rolls 196, 198 to absorbent core applicator 200. Arrow 201 indicates the direction of travel of absorbent core material 203 entering absorbent core applicator 200. Absorbent core applicator 200 includes a first conveyor 202 that advances absorbent core material 203 to pad cut-off device 206. Pad cut-off device 206 includes rotary knife roll 209 and rotary anvil roll 208. Knife roll 209 has a blade 207 extending across the roll transverse to the path of travel of absorbent core material 203. Knife roll 209 severs the absorbent core material across its length to form absorbent cores 13. A respective absorbent core 13 advances to second conveyor 204 Second conveyor 204 operates at a greater speed than first conveyor 202 and spaces apart consecutive absorbent cores 13 exiting pad cut-off device 206. While knife roll 209 has been disclosed as the preferred cutting device, other well known conventional absorbent core material cutting devices are well within the scope of the invention.

After conveyor 204 places absorbent core 13 adjacent bodyside liner 12, folding device 210 folds outside edges of continuous bodyside liner 12 over the absorbent core. After folding, bodyside liner 12 preferably extends over the top of absorbent core 13 by a distance of approximately one inch.

Glue gun 212 then applies adhesive to bodyside liner 12 as the elements advance. Base structure 154 enters nip 214 between rotary anvil roils 216, 218. Rolls 216, 218 of nip 214 rotate at a first surface speed that is faster than the surface speed of rotation of rolls 222, 224 at second nip 220 spaced downstream therefrom. The speed differential between first nip 214 and second nip 220 causes base structure 154 to ruffle or bunch up. First anvil rolls 216, 218 preferably operate at about 1.25 times the speed of second rotary anvil rolls 222, 224 of second nip 220. Second nip 220 secures ruffled base structure 154 to bodyside liner 12 with absorbent core 13 therebetween. Absorbent core 13 generally does not cover the entire surface area of base structure 154 or bodyside liner 12. Base structure 154 comprising substrate portions 50A, 50B and second substrate 136 extends beyond bodyside liner 12 and even outer cover 14.

While having the speed of rolls at first nip 214 faster than the speed at second nip 7220 is preferred, the speeds can also be substantially the same. In that instance, nip 214 and anvil rolls 216, 218 are not required. Furthermore, elastomeric element cutter 168 is not required because elastomeric elements 54 can be severed when web sausage 22 forms individual absorbent articles 35.

While glue gun 212 is shown applying adhesive to bodyside liner 12, the glue gun can be repositioned for applying adhesive to base structure 154.

Figure 15:
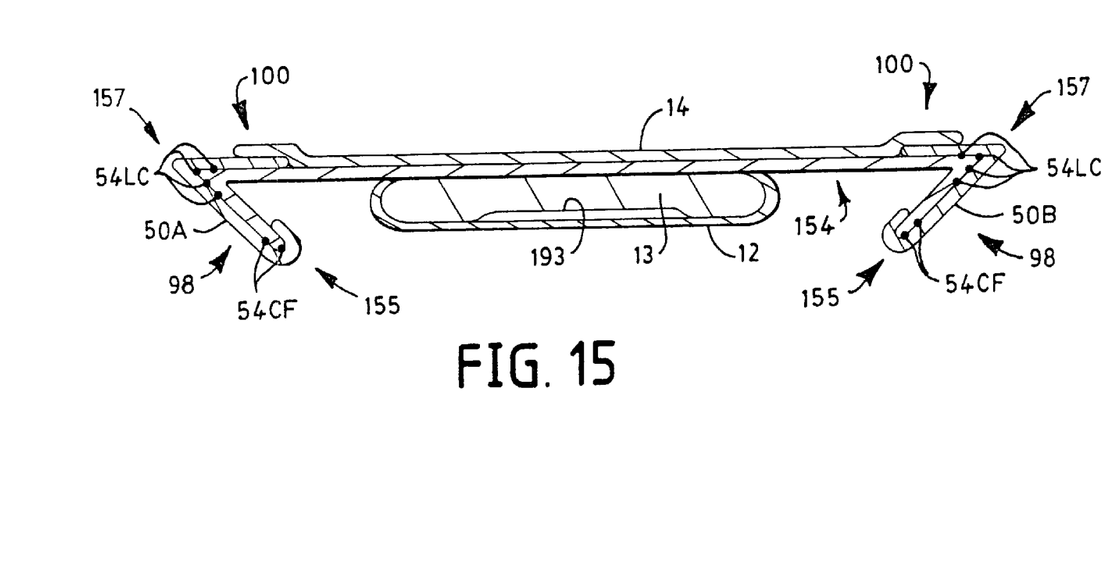
FIG. 15 shows a cross-sectional view of a web sausage formed by the apparatus and methods of the invention and taken at 15—15 of FIG. 12.

From second nip 220, the combination bodyside liner 12 and base structure 154 advance to folding device 226. Folding device 225 inwardly folds outside edges 155 of base structure 154 to form containment flaps 98 as shown in FIGS. 14 and 15. Ultrasonic bonder 228 bonds base structure 154 to itself to retain containment flaps 98 in the desired orientation shown in FIG. 15. Ultrasonic bonder 228 includes rotary anvil rolls 230 and ultrasonic horns 232. Ultrasonic horns 232, as shown in FIG. 12 send ultrasonic energy to the two facing portions of base structure 154 to retain fold 157 of respective containment flaps 98. Desirably, ultrasonic horns 232 operate at 20 KHz.

FIG. 15 is not drawn to scale. The size or width of many elements has been enlarged for purposes of illustration.

The combination of base structure 154/bodyside liner 12 turns on turning roll 234 and meets outer cover 14 including ears 34 at compression nip device 236. Compression nip device 236 includes anvil rolls 238, 240 that compress outer cover 14 to base structure 154. Glue gun 140 applies adhesive to outer cover 14. Further, glue gun 140 can be positioned to provide adhesive only to base structure 154, instead of outer cover 14. In this manner, web sausage 22 is formed as shown in FIG. 15. Web sausage 22 then advances along the direction shown by arrow 242 to another work station. Other possible work stations include waist piece applicators or the like.

Web sausage 22 eventually is cut into absorbent articles 35. This cutting can be done by any of a variety of well known cutting machines. For example, a final cut-off roll (not shown) having a knife (not shown) extending across the roll, in combination with an anvil roll (not shown) can sever web sausage 22. Absorbent articles 35 severed from web sausage 22 are transferred by conveyor to a stacker (not shown).

Elastomeric elements 54 preferably comprise continuous strands, ribbons, or one or more layers of a polymeric and/or elastomeric material, such as a rubber material, which is adhered to substrate portions 50A, 50B in a stretched condition. Elastomeric elements 54 can also comprise materials set forth with respect to leg cuff pieces 80 in the first embodiment of the invention. Elastomeric elements 54CF, as shown in FIG. 15, are located at respective outward edges of base structure 154. Elastomeric elements 54CF can provide the elastic properties of containment flaps 98 by moving flaps 98 away from absorbent article 35 and into contact with a users body.

Leg cuffs 100 ensure proper fitting of absorbent article 35 to a users body. Elastomeric elements 54LC, located inwardly from the outward edges of base structure 154, provide elastic properties of leg cuffs 100. As shown in FIG. 15, leg cuffs 100 are preferably formed by ribbons or strands 54LC along the lower inward portion of substrate portions 50A, 50B. These ribbons or strands 54LC are only glued or otherwise secured to base structure 154 in areas which will be near leg cut-outs 30 in the assembled absorbent article 35.

Elastomeric elements 54CF for containment flaps 98 preferably are stretched to a higher percentage of their stretch-to-stop distance than elastomeric elements 54LC which elasticize leg cuffs 100, whereby the containment flaps 98 extend outwardly toward the user's body. While two elastomeric elements 54CF are shown for containment flaps 98 and four elastomeric elements 54LC are shown for leg cuffs 100, any number of the respective elastomeric elements can be used for the containment flaps or the leg cuffs.

The various paths and sections of absorbent article assembly system 8 in FIG. 12 operate simultaneously at controlled speeds to form absorbent articles. The various devices can be controlled by a central controller (not shown), such as a digital or analog control system to ensure proper operation and timing for each device in each material operating path.

Furthermore, the devices can be modified as appropriate. For instance, ultrasonic bonders 120, 162, and 228 can be replaced with other known bonding devices utilizing gluing, stitching or any other well known method of securing elements.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. A method of making an absorbent article having a front portion and a back portion, and a crotch portion between the front portion and the back portion, the method comprising:
   (a) slitting a first elongate substrate into first and second separate pieces of material, having first and second lengths and first and second widths, and facing inner slit edges, and spacing the first and second separate pieces of material transversely from each other such that the facing inner slit edges are spaced from each other;

(b) securing, to the first and second separate pieces of material, a second elongate substrate, having a third length aligned with the first and second lengths of the first and second separate pieces of material, and a third width aligned with the first and second widths of the first and second separate pieces of material, such that a central region of the second substrate is disposed between the facing inner slit edges, and securing outwardly-disposed elastic elements between the second substrate and the first and second separate pieces of material, whereby the second substrate and the first and second separate pieces of material, in combination with the elastic elements, define a base structure wherein first and second opposing surfaces of the second substrate define portions of first and second opposing outer surfaces of the base structure between the first and second separate pieces of material;

(c) securing an absorbent core and a bodyside liner to the base structure at the first surface of the second substrate; and (d) securing an outer cover to the base structure, including securing a first portion of a width of the outer cover to the second surface of the second substrate, and securing second and third portions of the width of the outer cover to the first and second separate pieces of material, the first and second separate pieces of material, being between the outer cover and the second substrate.

2. A method as in claim 1, the base structure having a main body extending along the first, second, and third lengths, and opposing outside edge portions comprising outer edge portions of the first and second separate pieces of material, the method including folding the outer edge portions of the first and second separate pieces of material inwardly into J-shapes to face unfolded portions of the second substrate, with the second substrates of the base structure being between the folded outside edges and the elastic elements, the method further comprising bonding such outer edge portions to the second substrate.

3. A method as in claim 1, including folding opposing edge portions of the base structure inwardly and around the absorbent core.

4. A method as in claim 1, including cutting absorbent core material to form the absorbent core, and folding the bodyside liner around at least a portion of the absorbent core before securing the bodyside liner to the base structure.

5. A method as in claim 1, including drawing the base structure through a first nip at a first speed, and drawing the base structure through a second nip, rolls of the second nip operating at a second speed slower than the first speed, thereby forming ruffles in the base structure between the first and second nips, the second nip securing the bodyside liner and the absorbent core to the base structure.

6. A method as in claim 1, including, with the elastic elements disposed between the second substrate and the first and second separate pieces of material, crushing and weakening the elastic elements so as to break the elastic elements without damaging the second substrate, or the first or second separate pieces of material.

7. A method as in claim 1, and wherein, at the crotch portion, portions of the first, second, and third widths of the second substrate and the first and second portions of the first substrate, bearing ones of the elastic elements, extend from outer edges of the outer cover.

8. A method of making an absorbent article, comprising:

(a) bringing a first substrate, having first and second portions, comprising first and second separate pieces of material, and corresponding first and second lengths, and first and second widths, into facing relationship with a second substrate, the second substrate having a third length aligned with the first and second lengths, and a third width aligned with the first and second widths, the first and second portions of the first substrate being transversely spaced from each other, and thereby defining mutually facing portions of the second substrate and the first portion of the first substrate, and mutually facing portions of the second substrate and the second substrate portion of the first substrate;

(b) bringing together the mutually facing portions of the second first substrate and the first and second portions of the first substrate, and securing the mutually facing portions each other to form a base structure, with a plurality of elastic elements secured between the mutually facing portions, the elastic elements being aligned with the third first length and spaced transversely across the third width, and wherein the entirety of the widths of the mutually facing elements of the second substrate and the first and second portions of the first substrate are in direct securing contact with each other;

(c) securing an absorbent core and a bodyside liner to the base structure; and (d) securing an outer cover to the base structure, the first and second separate pieces of material, being between the outer cover and the second substrate.

9. A method as in claim 8, base structure having a main body extending along at least one of the first, second, and third lengths, opposing outside edge portions, and opposing outside edges of the base structure on the outside edge portions, the method including folding the outside edges of the base structure inwardly into J-shapes to face unfolded portions of the second substrate, with elastic elements, and bonding the outside edges to the unfolded portions of the second substrate.

10. A method as in claim 8, including folding opposing edge portions of the base structure to form folded edges of the base structure, folding the folded edges around the absorbent core, and bonding the folded edges in an inwardly folded direction.

11. A method as in claim 8, including cutting absorbent core material to form the absorbent core, and folding the bodyside liner around at least a portion of the absorbent core before securing the bodyside liner to the base structure.

12. A method as in claim 8, including drawing the base structure through a first nip at a first speed, then drawing the base structure through a second nip, rolls of the second nip operating at a second speed slower than the first speed, thereby forming ruffles in the base structure between the first and second nips, the second nip securing the bodyside liner and absorbent core to the base structure.

13. A method as in claim 8, including, with the plurality of elastic elements disposed between the second substrate and the first and second portions of the first substrate, severing the plurality of elastic elements without damaging the second substrate or the first or second portions of the first substrate.

* * * * *